United States Patent [19]

Obermeier et al.

[11] Patent Number: 5,015,728
[45] Date of Patent: May 14, 1991

[54] PROCESS FOR THE PREPARATION OF INSULIN DERIVATIVES, THE B CHAIN OF WHICH IS LENGTHENED C-TERMINALLY

[75] Inventors: Rainer Obermeier, Hattersheim am Main; Rolf Geiger, Frankfurt am Main; Ulrich Grau, Hofheim am Taunus, all of Fed. Rep. of Germany

[73] Assignee: Hoechst Aktiengesellschaft, Frankfurt am Main, Fed. Rep. of Germany

[21] Appl. No.: 172,236

[22] Filed: Mar. 23, 1988

Related U.S. Application Data

[63] Continuation-in-part of Ser. No. 650,639, Sep. 14, 1984, abandoned.

[30] Foreign Application Priority Data

Sep. 17, 1983 [DE] Fed. Rep. of Germany ....... 3333640

[51] Int. Cl.$^5$ ................................................ C07K 7/40
[52] U.S. Cl. ..................................... 530/303; 530/305
[58] Field of Search ...................... 530/303, 305; 514/3

[56] References Cited

U.S. PATENT DOCUMENTS

| | | | |
|---|---|---|---|
| 3,801,564 | 4/1974 | Geiger | 530/303 |
| 4,029,642 | 6/1977 | Obermeier | 530/303 |
| 4,320,196 | 3/1982 | Morihara | 514/3 |
| 4,320,197 | 3/1982 | Morihara | 514/3 |
| 4,511,505 | 4/1985 | Morihara | 530/303 |
| 4,601,852 | 7/1986 | Obermeier | 530/303 |
| 4,639,333 | 1/1987 | Obermeier et al. | 530/303 |
| 4,645,740 | 2/1987 | Breddam | 435/71 |

FOREIGN PATENT DOCUMENTS

| | | |
|---|---|---|
| 1173388 | 8/1984 | Canada . |
| 0017938 | 5/1981 | European Pat. Off. . |
| 0046979 | 3/1982 | European Pat. Off. . |
| 2005658 | 9/1971 | Fed. Rep. of Germany . |
| 2460753 | 6/1976 | Fed. Rep. of Germany . |
| 3209184 | 9/1983 | Fed. Rep. of Germany . |

OTHER PUBLICATIONS

Chance, R. E., Excerpta Med. Intl. Congr. Ser. No. 231, pp. 292–305.
Rose, K. et al., Biochem. J., 211:671–676 (1983).

*Primary Examiner*—F. T. Moezie
*Attorney, Agent, or Firm*—Finnegan, Henderson, Farabow, Garrett, and Dunner

[57] ABSTRACT

The invention relates to a process for the preparation of an insulin derivative of the formula I

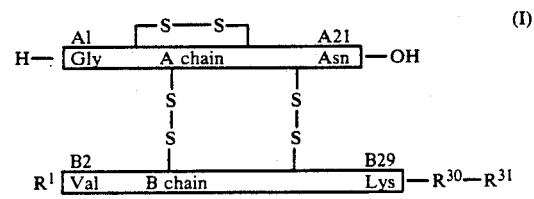

in which $R^1$ denotes H or H-Phe, $R^{30}$ represents the radical of a naturally occurring L-aminoacid and $R^{31}$ represents a physiologically acceptable organic group of neutral or basic character consisting of 1 to 3 α-aminoacids in which the terminal carboxyl function is present in the free form and which insulin derivative has an isoelectric point above 5.8, which comprises reacting an insulin of the formula I in which $R^{30}$ denotes the radical of a genetically codable L-aminoacid and $R^{31}$ represents OH or a protective group of the carboxyl function, with a peptide or aminoacid derivatives of the formula R-$R^{30}$-$R^{31}$ consisting of 2 to 4 α-aminoacids, in which the terminal carboxyl function is in free form, in the presence of a trypsin-like endopeptidase at a pH value below the isoelectric point of the starting insulin.

9 Claims, No Drawings

PROCESS FOR THE PREPARATION OF INSULIN DERIVATIVES, THE B CHAIN OF WHICH IS LENGTHENED C-TERMINALLY

This application is a continuation-in-part of Serial No. 650,639, filed Sept. 14, 1984; now abandoned.

BACKGROUND OF THE INVENTION

Insulin-Arg$^B$31-OH, insulin-Arg$^B$31-Arg$^B$32-OH and other insulins modified C-terminally by bases in the B chain exhibit depot character in drugs without specific additives, such as Surfen$^R$ or protamine. Such insulins, processes for their preparation, agents containing them and their uses have already been proposed (German Patent Applications P 33 26 472.4, P 33 26 473.2, P 33 27 709.5 and P 33 27 928.4). The advantages of such delayed-action insulin formulations are better tolerance and, in particular, in the case of the long-term treatment associated with insulin treatment, the absence of immunogenicity of the depot auxiliary.

In the biosynthesis of insulin, the double-chain insulin is formed from the immediate precursor, the single-chain proinsulin, by enzymatic detachment of the so-called connecting peptide. However, very small amounts of so-called intermediate insulins are also to be found in the crude insulin, isolated as a result of incomplete processing. The structures of these intermediates of insulin biosynthesis have been clarified. They consist predominantly of B31-Arg- and B31-32-Arg-Arg-insulin derivatives.

If proinsulins from cattle, pigs or humans are treated in vitro with trypsin (Chance, Excerpta Medica International Congress Series No. 231, page 292 et seq.), a mixture of B31-Arg-and B32-Arg-Arg-insulins in particular is formed, besides the corresponding desoctapeptide-B23-30-insulins. Reliable separation and high purification of these products is very expensive and requires several ion exchange chromatography steps, which results in product loss. Isolation of preparative amounts from crude insulin for use in therapy is thus not practicable. In addition, the products corresponding to human insulin are not available.

A possible way of isolating such derivatives consists in enzymatically splitting proinsulin, or analogs thereof, prepared by genetic engineering. As mentioned, losses arise from the purification process.

The object of the present invention is to describe a process in which those amounts of insulin derivatives modified by bases which are required for therapeutic use of the novel galenical formulations can be prepared in a simple manner.

The process according to the invention described below achieves the object by enzyme-catalyzed conversion of inexpensive biosynthetic insulin, such as human insulin, or porcine insulin, using suitable peptides to give the desired products.

SUMMARY OF THE INVENTION

In recent years, various chemical and enzymatic processes have been disclosed (Biochem. J. 211 (1983) 671-676, U.S. Pat. Nos. 3,903,068, 3,276,961, and 4,320,197, British Patent A-2,069,502 and European Patent A-56,951, and the like), with the aid of which, for example, porcine insulin can be converted. Moreover, processes have also been proposed which allow conversion of suitable preproinsulin derivatives and intermediate insulin, for example, into human insulin (German Patent Application P 32 09 184.2).

DETAILED DESCRIPTION OF THE PREFERRED EMBODIMENTS

It has now been found, surprisingly, that selective transamidations on the lysine radical in position B29 of insulin itself with peptides containing Arg or Arg-Arg, and despite the presence of Arg in position B22 of the insulin, result in high yields.

The invention relates to a process for the preparation of an insulin derivative of the formula I

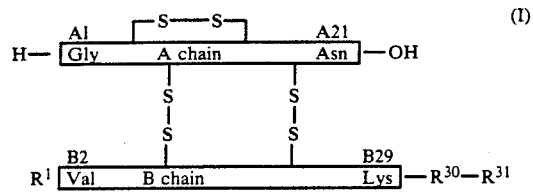

by reacting an insulin of formula II

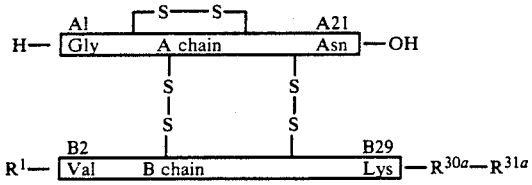

with a peptide of formula III $$H-R30-R-\qquad\qquad (III)$$

wherein said insulin derivative I, has an isoelectric point of above about 5.8, and R1 denotes H or H-Phe, R30 represents a radical of a neutral or basic naturally occurring L-amino acid, R31 represents a physiologically acceptable organic group of neutral or basic character, consisting of 1 or 3 α-amino acids in which the terminal carboxyl function is present in free form, wherein at least one of R30 and R31 is of a basic character, R30a denotes a radical of a genetically codable L-amino acid and R31a represents OH or a protective group of a carboxyl function, present in the free form, in the presence of a trypsin-like endopeptidase in water, if appropriate with the addition of a suitable organic solvent at a pH value below the isoelectric point of the starting insulin, preferably below pH 5.4.

Compounds which are prepared in particular are those of the formula I in which R1 represents H-Phe and/or R30 denootes Ala, Thr or Ser. Compounds in which the A chain and the Chain (B2-30) have the sequence of human insulin are preferably prepared.

Preferred starting compounds of the formula III are those which contain the sequence

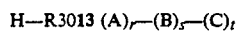

wherein

R30 denotes Ala, Thr, Ser, Leu or side-chain protected Lys, A and B are identical or different and represent L- and/or D-Arg, D-Lys, or side-chain protected Lys, C denotes L- or D-Arg, D-Lys, side-chain protected Lys, and r, s and t are identical or different and denote 0 or 1, and $r+s+t \geq 1$.

The following derivatives can be prepared, for example, by the processes according to the invention:
des-Phe$^{B}$1-porcine insulin-Arg$^{B}$31—OH
des-Phe$^{B}$1-human insulin-Arg$^{B}$31—OH
des-Phe$^{B}$1-porcine insulin-Arg$^{B}$31-Arg$^{B}$32-OH
des-Phe$^{B}$1-human insulin-Arg$^{B}$31-Arg$^{B}$32-OH
des-Thr$^{B}$30-human insulin-Val$^{B}$30-Ala$^{B}$31-Arg$^{B}$32-OH
Human insulin-Lys$^{B}$31-OH
Human insulin-D-Arg$^{B}$31-OH
Human insulin-D-Arg$^{B}$31-Arg$^{B}$32-OH
Human insulin-Arg$^{B}$31-D-Arg$^{B}$32-OH
Human insulin-Lys$^{B}$31-Arg$^{B}$32-OH
Human insulin-Arg$^{B}$31-Lys$^{B}$32-OH
Human insulin-Val$^{B}$31-Arg$^{B}$32-OH
Human insulin-Val$^{B}$31-Arg$^{B}$32-Arg$^{B}$33-OH
Human insulin-Lys$^{B}$31-Arg$^{B}$32-Arg$^{B}$33-OH
Human insulin-Orn$^{B}$31-OH
Human insulin-Leu$^{B}$31-Cit$^{B}$32-OH
des-Thr$^{B}$30-human insulin-Arg$^{B}$30-Arg$^{B}$31-OH
des-Thr$^{B}$30-human insulin-Lys$^{B}$30-Ala$^{B}$31-Arg-B32-OH and in particular
Human insulin-Arg$^{B}$31-OH
Human insulin-Arg$^{B}$31-Arg$^{B}$32-OH.

The following L-amino acids are genetically codeable: Gly, Ala, Ser, Thr, Val, Leu, Ile, Asp, Asn, Glu, Gln, Cys, Met, Arg, Lys, His, Tyr, Phe, Trp and Pro (neutral aminoacids underlined).

A neutral, naturally occurring amino acid is understood, in particular, as meaning Gly, Ala, Ser, Thr, Val, Leu, Ile, Asn, Gln, Cys, Met, Tyr, Phe, Pro or Hyp. A basic, naturally occurring amino acid is understood, in particular, as meaning Arg, Lys, Hyl, Orn, Cit or His.

Insulins which can be used as starting materials are all the insulins isolated naturally containing Lys (B29), but preferably those from pigs and humans. Des-Phe$^{B}$1-insulins as starting compounds for the process according to the invention are known, for example, from German Patent 2,005,658 or from European Patent A-46,979.

Peptides or amino acid derivatives which can be used for the enzyme-catalyzed reaction are, in particular, all the di-, tri- and tetra-peptides which, if appropriate, are protected in the side chain and have Gly, or L- or D-amino acids as the N-terminus. If necessary, the free side-chain COOH, -OH, -SH, -NH2, -guanidino and/or -imidazole groups present are protected in a manner which is known per se (cf., for example, Bodanszky et al. in Peptide Synthesis, 2nd Ed. (1976), John Wiley & Sons).

Examples of urethane-protective groups of the -amino function of Lys or Orn are Fmoc, Fcboc, Boc, Ddz, Adoc, and Msc. These amino-protective groups are removed with acids or bases (cf. Kontakte Merck 3/79, page 14 et seq.).

Examples of protective groups on the guanidino group of arginine are Adoc, Boc, and the like. These can be split off hydrolytically (cf. Kontakte Merck 1/80, pages 23, 30).

The COOH side function of Asp and Glu can be blocked in the form of an alkyl ester, preferably the methyl, ethyl or tert.-butyl ester. Deblocking is effected by alkaline or acid hydrolysis (cf. Kontakte Merck 3/79, pages 14, 20).

The OH side function of Thr or Ser can be blocked in a known manner by ether or acyl-protective groups, such as, for example, (C1 to C6)-alkyl, preferably tert.-butyl, or (C1 to C6)-alkanoyl.

The above-mentioned peptides or aminoacid derivatives are synthesized by standard processes, such as are described, for example, in "The Peptides Analysis, Synthesis, Biology, Vol. 1 Major Methods of Peptide Bond Formation, Part A", editors E. Gross and J. Meierhofer, Academic Press N.Y. (1979).

Those endopeptidases which are known from the literature as being trypsin-like, i.e. those which specifically split peptide bonds on the carboxyl end of basic amino acids, especially lysine (cf., for example, European Patent A-17,938) are suitable for the process according to the invention. The invention of European Patent A-17,938 relates to a semi-synthesis of human insulin. More particularly, it consists of an enzymatic synthesis of a B30-threonine-insulin including human insulin. The synthesis is effected to react a des-B30-insulin with an excess amount of a threonine derivative in the presence of an enzyme specifically acting on the basic-amino-acid carbonyl in peptide linkages and remove a protecting group of the threonine to yield a B30-threonine insulin. A preferred endopeptidase is lysyl endopeptidase.

The amino acid or peptide compounds used for the enzymatic conversion are preferably employed in a 40- to 150-molar excess, based on the insulin component. A weight ratio of the enzyme to the insulin component of preferably 1:5 to 1:20, in particular 1:10, can be used as the enzyme: substrate ratio.

In order to react peptide compounds according to the invention which have a relatively low water-solubility, a suitable water-miscible organic solvent, such as methanol, dimethylformamide or dioxane, can optionally be added to the otherwise aqueous reaction solution until a homogeneous solution is obtained.

The pH values at which the enzymatic reaction is carried out are usually between 4 and 5, and are preferably about pH 4.5. At pH values higher than those in the given range, the yields of the preferred transamidation reactions on position Lys$^{B}$29 are reduced by undesired proteolytic splitting.

The process of the invention works surprisingly with nonprotected or only side chain protected peptide starting materials in the presence of a trypsin-like endopeptidase with high yields, whereas with trypsin itself only low yields, if any, are obtained. Since no splitting off of terminal carboxyl group-protecting groups is necessary, the instant process avoids the degradation and decomposition which usually takes place during such splitting off.

It is a common factor of all the insulin derivatives prepared according to the process of the instant invention, that the additional positive charge(s) in the molecule impart(s) to the molecule an isoelectric point which is shifted into the neutral range. Isoelectric points of 5.8 to about 8.5, in particular 6.2 to 8.2, are measured by isoelectric focussing, depending on the derivative. The derivatives are thus (in the neutral range) less soluble than natural insulin or proinsulin, which have their isoelectric point and hence, range of maximum insolubility, at pH = 5.4 while they are usually in solution in the neutral range.

The insulin derivatives prepared by the process of the instant invention are used for the manufacture of aqueous solutions or suspensions of amorphous or crystalline precipitates of the derivatives in a physiologically acceptable excipient with an approximately neutral pH or other typical use forms for the treatment of diabetes mellitus.

The following examples are intended to serve to further illustrate the invention, without restricting the invention to these examples:

EXAMPLES

EXAMPLE 1

450 mg of crystalline porcine insulin were mixed with 3.7 g of (tert.-butyl)-threonyl-arginine and 1.5 ml of water, and the pH of the rather viscous solution was adjusted to 5.0 with triethylamine; the pH was measured by taking out 0.1 ml of the solution, diluting it with 0.2 ml of water and measuring with a glass electrode. To the reaction mixture 2 mg of a lysyl endopeptidase preparation were added, the activity of which was 10 units. The mixture was kept at room temperature for 4 days up to a conversion rate of 72% (measured with HPLC). Thereafter, the mixture was diluted with 50 ml of water and the human insulin-(tert.-butyl)-B30-Arg-B31, which had been formed, was precipitated together with the unreacted porcine insulin by means of the addition of 1 ml of a 1% aqueous $ZnCl_2$-solution at pH 6.3. The precipitate was separated by centrifuging, washed with a small amount of water and dried in vacuo. Yield: 420 mg.

In order to split off the tert.-butyl-protecting group in the side-chain of the threonine radical in the B30-position, the product was dissolved in 2 ml of trifluoroacetic acid, and kept for 45 minutes at room temperature. In order to isolate the insulin, 10 ml of diisopropylether were added to the solution. The precipitated insulin was separated by centrifuging, washed with diisopropylether and dried. The yield was 417 mg.

The Arg-B31-human insulin was separated from unreacted porcine insulin with the aid of a cation exchanger, and isolated from the corresponding fractions by means of usual crystallization procedures. The crystallized product was dried in vacuo; yield: 205 mg. The amino acid analysis gave the theoretical values, i.e. the values for the amino acids of the human insulin with an additional arginine radical.

EXAMPLE 2

Analogous to the procedure of Example 1, 500 mg of porcine insulin were mixed with 9.2 g of (tert.-butyl)-threonyl-argi- nyl-arginine =Thr(But)-Arg-Arg 5 ml of water and 20 enzyme units of lysyl endopeptidase, and the pH of the mixture was adjusted to 5.1. After 3 days a conversion rate of 50% was measured by means of HPLC.

The reaction was stopped as in Example 1 and the product was isolated; yield: 443 mg.

The splitting off of the tert.-butyl-protection group and the purification of the Arg2-B31-32-human insulin were performed as in Example 1. The yield of the desired product was 186 mg, the amino acid analysis of which corresponded to the theoretical values.

EXAMPLE 3

Analogous to Example 1, 500 mg of porcine insulin were mixed with 5.0 g of Thr-Arg, 6 ml of water and 10 enzyme units of lysyl endopeptidase, and the pH of the mixture was adjusted to 5.0.

The working-up, and the purification of the reaction product were performed in the same manner as in the preceeding Examples. The yield obtained was 250 mg of a highly purified Arg-B31-human insulin, the amino acid analysis of which corresponded to the theoretical values.

We claim:

1. A process for the preparation of an insulin derivative of formula I comprising an aqueous solvent reacting, in ndopeptidase and an insulin of formula II

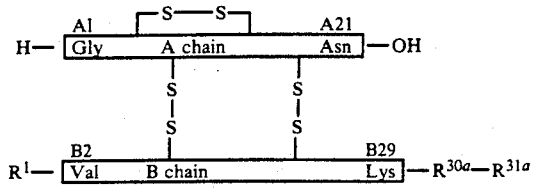

with a peptide of formula III

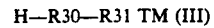

$$H-R30-R31 \ TM \ (III)$$

to produce the insulin derivative of formula I

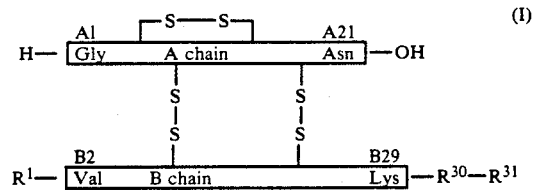

wherein said insulin derivative I has an isoelectric point of above about 5.8, and $R^1$ denotes H or H-Phe, $R^{30}$ represents a radical of a neutral or basic naturally occuring L-amino acid, $R^{31}$ represents a physiologically acceptable organic group of neutral or basic character, consisting of 1 to 3 α-amino acids in which the terminal carboxyl function is present in a free form, wherein at least one of $R^{30}$ and $R^{31}$ is of a basic character, $R^{30a}$ denotes a radical of a genetically codable L-amino acid and $R^{31a}$ represents OH or a protective group of a carboxyl function.

2. A process as claimed in claim 1, wherein said lysyl endopeptidase is in an enzyme solvent selected from the group consisting of (a) water and (b) water and an organic solvent, wherein said enzyme solvent is at a pH value below about the isoelectric point of the insulin-derivative I, 3. A process as claimed in claim 1, wherein $R^1$ is H-Phe.

4. A process as claimed in claim 1, wherein $R^1$ is H.

5. A process as claimed in claim 1, wherein $R^{30}$ is selected from the group consisting of Ala, Thr and Ser.

6. A process as claimed in claim 1, wherein formula II represents human insulin.

7. A process as claimed in claim 1, wherein formula I represents human insulin-$Arg^{B31}$—OH or human insulin-$Arg^{B31}$—$Arg^{B32}$—OH.

8. A process as claimed in claim 1, wherein said peptide of formula III comprises a peptide of formula IV

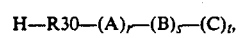

$$H-R30-(A)_r-(B)_s-(C)_t,$$

wherein

R30 is an amino acid selected from the group consisting of Ala, Thr, Ser. Leu and side-chain protected Lys, A and B are identical or different and each is selected from the group consisting of (a) at least one of L-Arg and D-Arg, (b) D-Lys and (c) a side-chain protected Lys, C is selected from the group consisting of L-Arg, D-Arg, D-Lys and a side-chain protected Lys, and r, s and t are identical or different and each denotes 0 or 1, wherein $r + s + t$ is equal to or greater than 1.

9. A process as claimed in claim 1, wherein said insulin of formula II is a porcine insulin.

* * * * *

UNITED STATES PATENT AND TRADEMARK OFFICE
CERTIFICATE OF CORRECTION

PATENT NO. :   5,015,728

DATED      :   May 14, 1991

INVENTOR(S) :  Rainer Obermeier

It is certified that error appears in the above-identified patent and that said Letters Patent is hereby corrected as shown below:

In the Abstract, Line 13, change "L-aminoacid" to --L-amino acid--;

Line 16, change "aminoacids" to --amino acids--;

Line 20, change "L-aminoacid" to --L-amino acid;

Line 22, change "aminoacid" to --amino acid--;

Line 22, change "derivatives" to --derivative--;

Line 23, change "α-aminoacids" to --αamino acids--;

UNITED STATES PATENT AND TRADEMARK OFFICE
CERTIFICATE OF CORRECTION

PATENT NO. : 5,015,728

DATED : May 14, 1991

INVENTOR(S) : Rainer Obermeier

It is certified that error appears in the above-identified patent and that said Letters Patent is hereby corrected as shown below:

Claim 1, Column 6, Line 5, delete "an aqueous solvent";

Column 6, Line 6, after "in" insert --an aqueous solvent, lysyl--;

Column 6, Line 6, change "ndopeptidase" to --endopeptidase--;

Column 6, Line 18, change "H-R30-R31 TM (III)" to --H-$R^{30}$-$R^{31}$ (III)--;

Column 6, Line 36, change "occuring" to --occurring--;

Column 6, Line 40, after "in" delete "a";

Claim 2, Column 6, Line 50, after "insulin" delete " - ";

Column 6, Line 51, after "I" change " , " to -- . --;

UNITED STATES PATENT AND TRADEMARK OFFICE
CERTIFICATE OF CORRECTION

PATENT NO. : 5,015,728
DATED : May 14, 1991
INVENTOR(S) : Rainer Obermeier

It is certified that error appears in the above-identified patent and that said Letters Patent is hereby corrected as shown below:

Claim 7, Column 6, Line 61, change "$Arg^B 31$" to --$Arg^{B31}$--;

Column 6, Line 62, change "$Arg^B 31-Arg^B 32$" to --$Arg^{B31}-Arg^{B32}$--;

Claim 8, Column 6, Line 66, change "R30" to --$R^{30}$--;

Column 7, Line 1, change "R30" to --$R^{30}$;

Column 7, Line 2, after "Ser" change " . " to -- , --.

Signed and Sealed this

Nineteenth Day of January, 1993

*Attest:*

DOUGLAS B. COMER

*Attesting Officer*    Acting Commissioner of Patents and Trademarks